(12) United States Patent
Kawabata (10) Patent No.: US 7,210,355 B2
(45) Date of Patent: May 1, 2007

(54) SUPERSONIC SENSOR HEAD FOR SUPERSONIC NON-DESTRUCTIVE TEST APPARATUS

(75) Inventor: Shinya Kawabata, Tokyo (JP)

(73) Assignee: Fuji Jukogyo Kabushiki Kaisha, Tokyo (JP)

( * ) Notice: Subject to any disclaimer, the term of this patent is extended or adjusted under 35 U.S.C. 154(b) by 183 days.

(21) Appl. No.: 11/064,181

(22) Filed: Feb. 23, 2005

(65) Prior Publication Data
US 2005/0183506 A1 Aug. 25, 2005

(30) Foreign Application Priority Data
Feb. 25, 2004 (JP) .............................. 2004-049407

(51) Int. Cl.
*G01N 29/28* (2006.01)
(52) U.S. Cl. ........................................................ 73/644
(58) Field of Classification Search ................. 73/644; 600/459
See application file for complete search history.

(56) References Cited

U.S. PATENT DOCUMENTS 3,394,586 A * 7/1968 Cross ........................... 73/644

5,078,149 A * 1/1992 Katsumata et al. ........... 73/644

FOREIGN PATENT DOCUMENTS

JP 57-113692 A * 7/1982
JP 2002-181796 6/2002

* cited by examiner

*Primary Examiner*—John E. Chapman
(74) *Attorney, Agent, or Firm*—Smith, Gambrell & Russell (57) ABSTRACT

A supersonic sensor head for a supersonic non-destructive test apparatus is disclosed. The supersonic sensor head includes a supersonic vibrator for transmitting and receiving supersonic waves, a holder having a base end and an opening end, and a soft gel material contact medium provided in the holder between the vibrator and a test object. The holder is coaxial with the vibrator so that the base end of the holder is in contact with a free end of the vibrator. By way of the contact medium, the supersonic vibrator indirectly contacts the test object. When a contact part of the contact medium is pressed against the test object, the vibrator comes into close contact with the contact medium, and the contact medium comes into close contact with the test object. The opening end of the holder restricts the deformation of the contact part of the contact medium.

20 Claims, 6 Drawing Sheets

Prior Art

FIG.6

Prior Art

FIG.7A

Prior Art

FIG.7B

Prior Art

FIG.7C

Prior Art

FIG.8A

Prior Art

FIG.8B

Prior Art

FIG.8C

Prior Art

SUPERSONIC SENSOR HEAD FOR SUPERSONIC NON-DESTRUCTIVE TEST APPARATUS

CROSS REFERENCE TO RELATED APPLICATIONS AND INCORPORATION BY REFERENCE

This application is based upon and claims the benefit of priority from the prior Japanese Patent Application No. 2004-049407, filed on Feb. 25, 2004; the entire content of which is incorporated herein by reference.

BACKGROUND OF THE INVENTION

1. Field of the Invention

The present invention relates to a supersonic sensor head for a supersonic a non-destructive test apparatus for examining a test object without destroying the same.

2. Discussion of the Related Art

In a method for manufacturing articles such as machines and structures, plates manufactured by deformation processing are welded to each other. The stability of the welded parts is sometimes confirmed by the non-destructive test when the welded structures are required to have a particularly high reliability.

As an apparatus for the non-destructive test, a supersonic non-destructive test apparatus is known. When the supersonic non-destructive test apparatus is used, a vibrator in the apparatus for outputting and inputting supersonic waves, is pressed to an object to be tested (test object) via a contact medium. More specifically, there are two non-destructive test methods, i.e. wet-type and dry-type methods for testing test objects.

Figure 5:
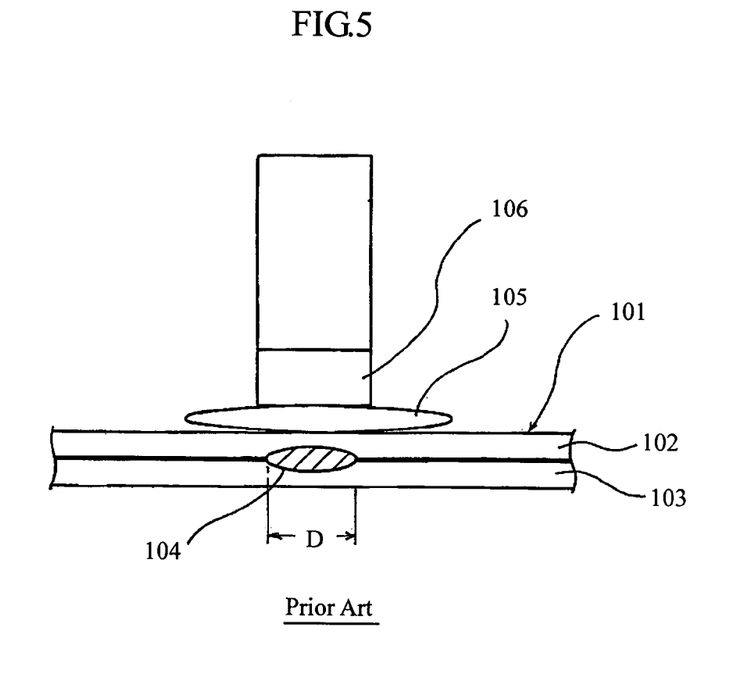
FIG. 5 is a diagram for explaining a conventional supersonic non-destructive apparatus.

An example of the wet-type supersonic non-destructive test method is shown by a diagram in FIG. 5. As shown the figure, an upper plate 102 and a lower plate 103 are welded to each other by spot welding, so that a test object is formed. A welded part 104 a in the test object 101 is tested by the supersonic non-destructive test method for determining the quality. For this purpose, a nugget diameter D of the welded part 104 is determined, and the stability (soundness) of the welding is judged from the measurement result.

For determining the nugget diameter D in the wet-type supersonic non-destructive test method, a liquid contact medium 105 such as water or oil is applied to a surface of the upper plate 102. The contact medium 105 plays a role as a supersonic wave propagation material. A supersonic vibrator 106 is pressed to the test object 101 so that the upper plate 102 and the supersonic vibrator 106 closely contacts each other via a film made of the liquid contact medium 105 provided therebetween. Supersonic wave is transmitted from the supersonic vibrator 106, reflected in the test object, and received by the vibrator 106. Accordingly, the nugget diameter D is determined from the difference of the forwarded and returned supersonic waveforms.

In the wet-type supersonic non-destructive test method, the close contact between the test object 101 and the vibrator 106 makes it possible for the vibrator to receive stable and large wave forms even, when the pressing force of the supersonic vibrator is small.

However, additional treatments are necessary for the wet-type test method. Namely, it is necessary to apply the liquid contact medium 105 to the surface of the test object 101 prior to the test, and to eliminate the contact medium 105 after the test. This operation is not easy. Moreover, the contact medium 105 sometimes cannot be completely removed. In such case, contact medium 105 left on the test object 101 will make the test object 101 unclean, and it is possible to form rust on the test object 101.

Figure 6:
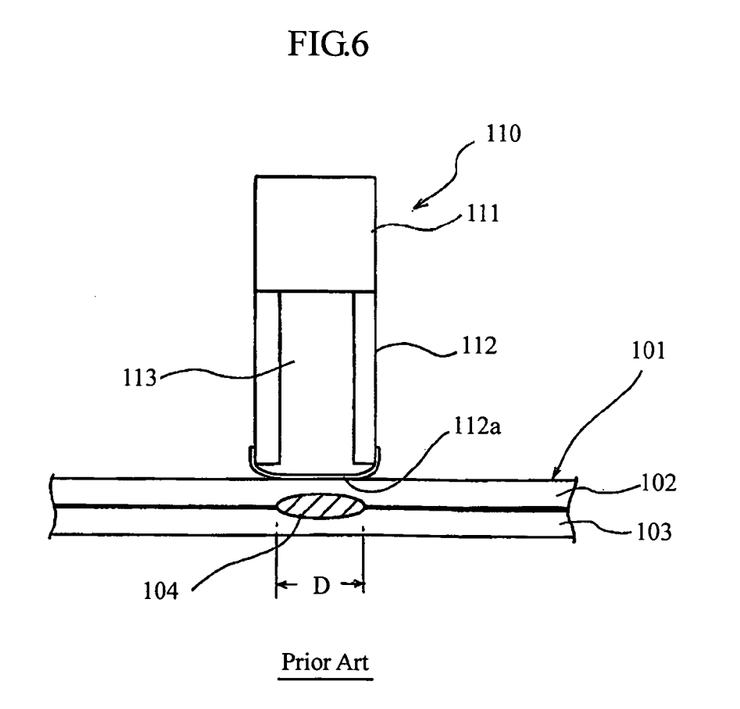
FIG. 6 is a diagram for explaining another conventional supersonic non-destructive apparatus.

An example of the dry-type supersonic non-destructive test method is shown by a cross-sectional diagram in FIG. 6. In the figure, the test object 101 including the upper and lower plates 102 and 103 is also prepared by spot welding. Then, the nugget diameter D of the welded part 104 is determined for confirming if the welding is firmly made.

In the dry-type method, a tube shaped body 112 with a bottom wall is provided on a free end of a supersonic vibrator 111. A free end 112a of the tube shaped body 112 is made of a flexible contact medium such as a thin rubber film. The space determined by the free end of the vibrator 111 and the tube shaped body 112 is filled with a liquid contact medium 113 such as water or oil as a supersonic propagation material. Accordingly, a supersonic sensor head 110 is structured. The test object is examined by closely applying the free end 112a of the tube shaped body 112 included in the supersonic sensor head 110. In the same way as in the wet-type method, a supersonic wave from the sensor head 110 goes forward and is reflected in the test object, so that the nugget diameter D is detected by the difference of forwarding and returning supersonic waveforms.

When the supersonic non-destructive apparatus shown in FIG. 6 is used, the free end 112a of the tube shaped body 112, which is made of the thin rubber film or the like, is largely deformed, and hence a contacting area between the free end 112a and the test object 101 changes. In accordance with the change of the surface area, the supersonic wave propagation area from the supersonic vibrator 111 to the test object 101 is also changed. Therefore, the test accuracy is affected. Moreover, it is difficult to maintain the durability of the free end 112a of the tube shaped body 112 made of a thin rubber film. Furthermore, it is not easy to fill the tube shaped body 112 with the liquid contact medium 113. As a result, working efficiency is not very good.

Figure 7A:
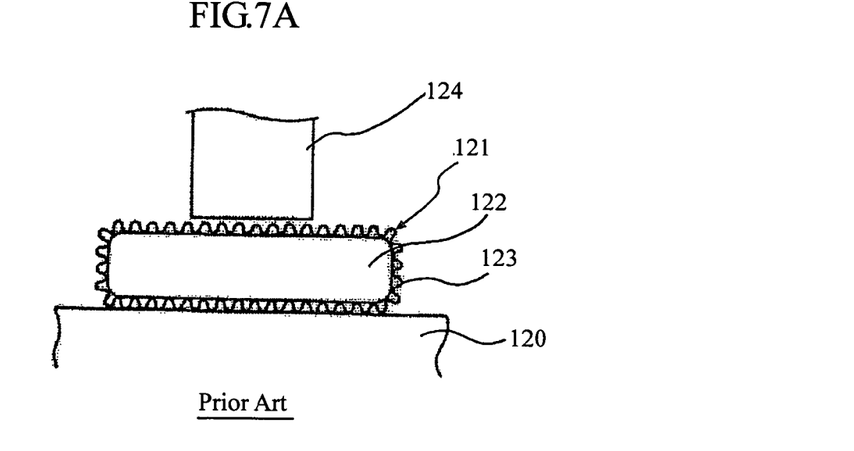
FIGS. 7A to 7C are diagrams for explaining a further conventional supersonic non-destructive apparatus.
Figure 7B:
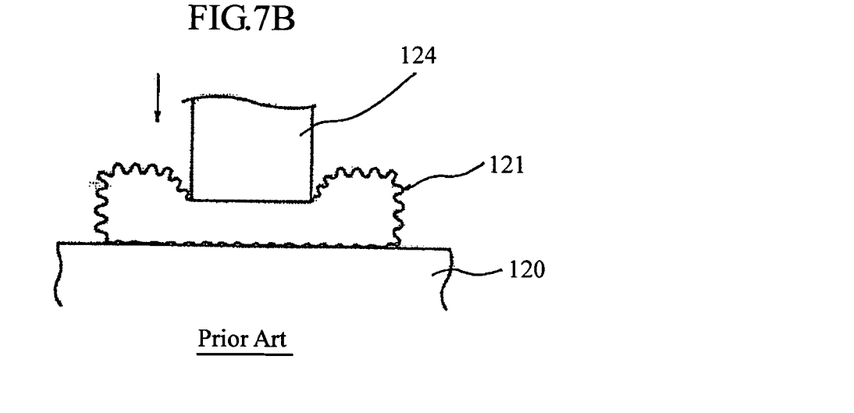
Figure 7C:
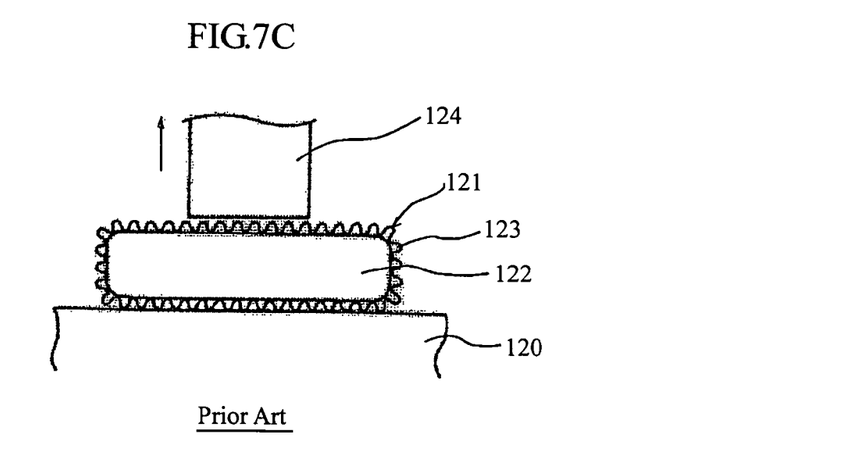

FIGS. 7A to 7C describe another example of the dry-type supersonic non-destructive test method. As shown in a cross section of FIG. 7A, the supersonic non-destructive test is also carried out by using a silicone rubber 122 which is a gel material with an excellent flexibility and restoration as a supersonic propagation material. The contact medium 121, as a supersonic propagation material, includes a silicone rubber 122 and a net 123 made of polypropylene with which the silicone rubber 122 is covered. The contact medium 121 is placed on the top surface of a test object 120. The contact medium 121 is interposed between a supersonic vibrator 124 and the test object 120. When the supersonic vibrator 124 is moved downwardly, the contact medium 121 is also pressed down. Therefore, the net 123 and the silicone rubber 122 are deformed. As a result, close contact is attained between the supersonic vibrator 124 and the contact medium 121, and between the contact medium 121 and the test object 120. In this state, the test object 120 is subjected to the supersonic non-destructive test by using the supersonic vibrator 124. After the test, the supersonic vibrator 124 is moved upwardly, and the contact medium 121 is brought back to have an original shape by the elastic restoring force of the silicone rubber 122 and the net 123, as shown in FIG. 7C (Japanese patent Kokai Publication 2002-181796).

Accordingly, the contact medium 121 is easily detached from the supersonic vibrator 124 and the test object 120. Moreover, the contact medium 121 can be repeatedly used because the net 123 provided on the silicone rubber 122 protects the surface thereof.

In this technology, however, a large cost is required for carrying out the test procedure. This is because the contact medium 121 has to be placed at a predetermined test position on a test object 120, and the contact medium 121 has to be collected after the test. Moreover, the contact medium 121 is largely deformed, so that a contacting area between the contact medium 121 and the test object 120 is changed. Accordingly, the supersonic wave propagation area from the supersonic vibrator 124 to the test object 120 is also changed. Therefore, the test accuracy is affected.

In addition to the above, it is possible that the net 123 on the silicone rubber 122 prevents the close contact between the supersonic vibrator 124 and the contact medium 121 and between the contact medium 121 and the test object 120. This could also affect the test accuracy.

Figure 8A:
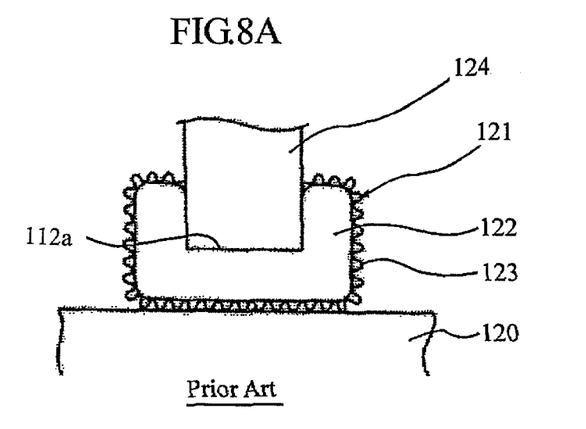
FIGS. 8A to 8C are diagrams for explaining a still another conventional supersonic non-destructive apparatus.

FIGS. 8A to 8C describe a further example of the dry-type supersonic non-destructive test method. As shown in the figure, a silicone rubber 122 has a receiving part 112a which has a shape for tightly accepting a free end of a supersonic vibrator 124. The receiving part 112a of the silicone rubber 122 is in close contact with the corresponding surface of the supersonic vibrator 124. The outer surface of the silicone rubber which is not in contact with the vibrator 124 is covered with a net 123. On the other hand, the surfaces of the silicone rubber 122 and the vibrator 124 which are in contact with each other are not covered with the net 123, for maintaining the close contact.

Figure 8B:
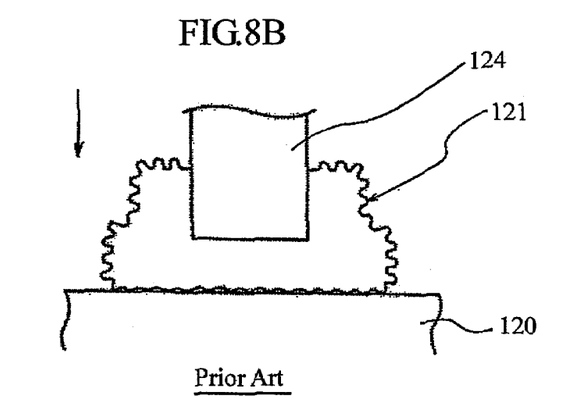

When the supersonic vibrator 124 is operated to press the contact medium 121, the contact medium 121 is deformed as shown in FIG. 8B. Accordingly, the contact medium 121 closely contacts the test object 120. In this state, the supersonic test is carried out. When the supersonic vibrator 124 is raised up after the test, the contact medium 121 is raised up together with the vibrator 124.

Figure 8C:
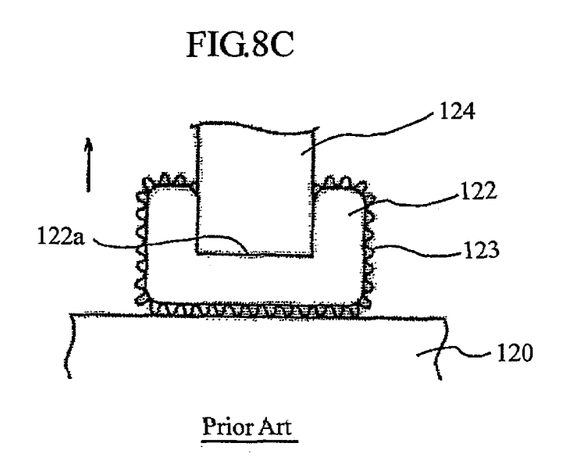

The elastic restoration force of the silicone rubber 122 and the net 123 makes it possible to easily loose the close contact between the test object 120 and the contact medium 122 as shown in FIG. 8C (Refer to Japanese Kokai Patent Application 2002-181796).

Japanese Kokai Patent Application 2002-181796 (FIGS. 8A to 8C) discloses that the contact medium 121 in the supersonic non-destructive test apparatus is always maintained to have a close contact state with the free end of the supersonic vibrator 124. Therefore, it is possible to omit an operation for placing the contact medium 121 at an appropriate position between the contact medium 121 and the test object 120.

However, the contact area between the contact medium 121 and the test object 120 changes because the shape of the contact medium 121 is largely changed. Depending on the change of the contact area, the supersonic propagation area from the supersonic vibrator 124 to the test object 120 is widely changed. Accordingly, the test accuracy is affected by the change. Moreover, the net 123 covering the silicone rubber 122 prevent the contact medium 121 and the test object 120 from closely contacting with each other. This also will affect the test accuracy.

OBJECT AND SUMMARY OF THE INVENTION

It is therefore a first object of the present invention to provide a supersonic sensor head for a supersonic non-destructive test apparatus for measuring shapes of supersonic waves transmitted in a test object, which has a simple structure and an excellent durability, and by which the test accuracy is stably obtained, comprising a supersonic vibrator for transmitting and receiving supersonic waves; a tube-shaped holder having a base end and an opening end, the holder being coaxial with the supersonic vibrator so that the base end of the holder is in contact with a free end of the supersonic vibrator; and a contact medium made of a soft gel material provided between the supersonic vibrator and the test object, so that the supersonic vibrator indirectly contact the test object, the contact medium having a basal part and a contact part, and being contained in the holder, the basal part contacting the free end of the supersonic vibrator and the contact part protruding from the opening end of the holder, a pressure applied between the contact part of the contact medium and the test object urging the free end of the supersonic vibrator to closely contact the basal part of the contact medium, and the contact part of the contact medium to closely contact the test object.

It is a second object of the present invention to provide a supersonic sensor head for a supersonic non-destructive test apparatus by which the contact medium is stably maintained and the supersonic wave is properly converged, wherein the holder is approximately cone-shaped, and the inner diameter of the cone decreasing from the base end to the opening end.

It is a third of the invention to provide a supersonic sensor head for a supersonic non-destructive test apparatus with which the test accuracy is improved, wherein the inner diameter of the holder at the opening end is approximately the same as a test diameter of the test object.

It is a fourth object of the invention to provide a supersonic sensor head for a supersonic non-destructive test apparatus with which many kinds of test objects having a variety of diameters can be tested, wherein the holder has a diameter converging mechanism for regulating the inner diameter of the holder at the opening end thereof.

It is a fifth object of the invention to provide a supersonic sensor head for a supersonic non-destructive test apparatus which is applicable to many kinds of tests, wherein the base end of the holder is detachably connected to the supersonic vibrator.

It is a sixth object of the invention to provide a supersonic sensor head for a supersonic non-destructive test apparatus by which the non-destructive test is performed by easily deforming the contact medium with application of a small pressure, wherein the soft gel material is a silicone rubber.

BRIEF DESCRIPTION OF THE DRAWINGS

A more complete appreciation of the invention and many of the attendant advantages thereof will be readily perceived as the same becomes better understood by reference to the following detailed description when considered in connection with the accompanying drawings, wherein.

DETAILED DESCRIPTION OF THE INVENTION

Other features of this invention will become apparent in the course of the following description of exemplary embodiments, which are given for illustration of the invention and are not intended to be limiting thereof.

A supersonic sensor head of the invention used for a supersonic non-destructive apparatus will now be explained by referring to figures. In the following embodiments, a test object is obtained by subjecting two plates to spot welding. The stability of the weld is examined by detecting the nugget diameter by the supersonic non-destructive apparatus.

(First Embodiment)

Figure 1:
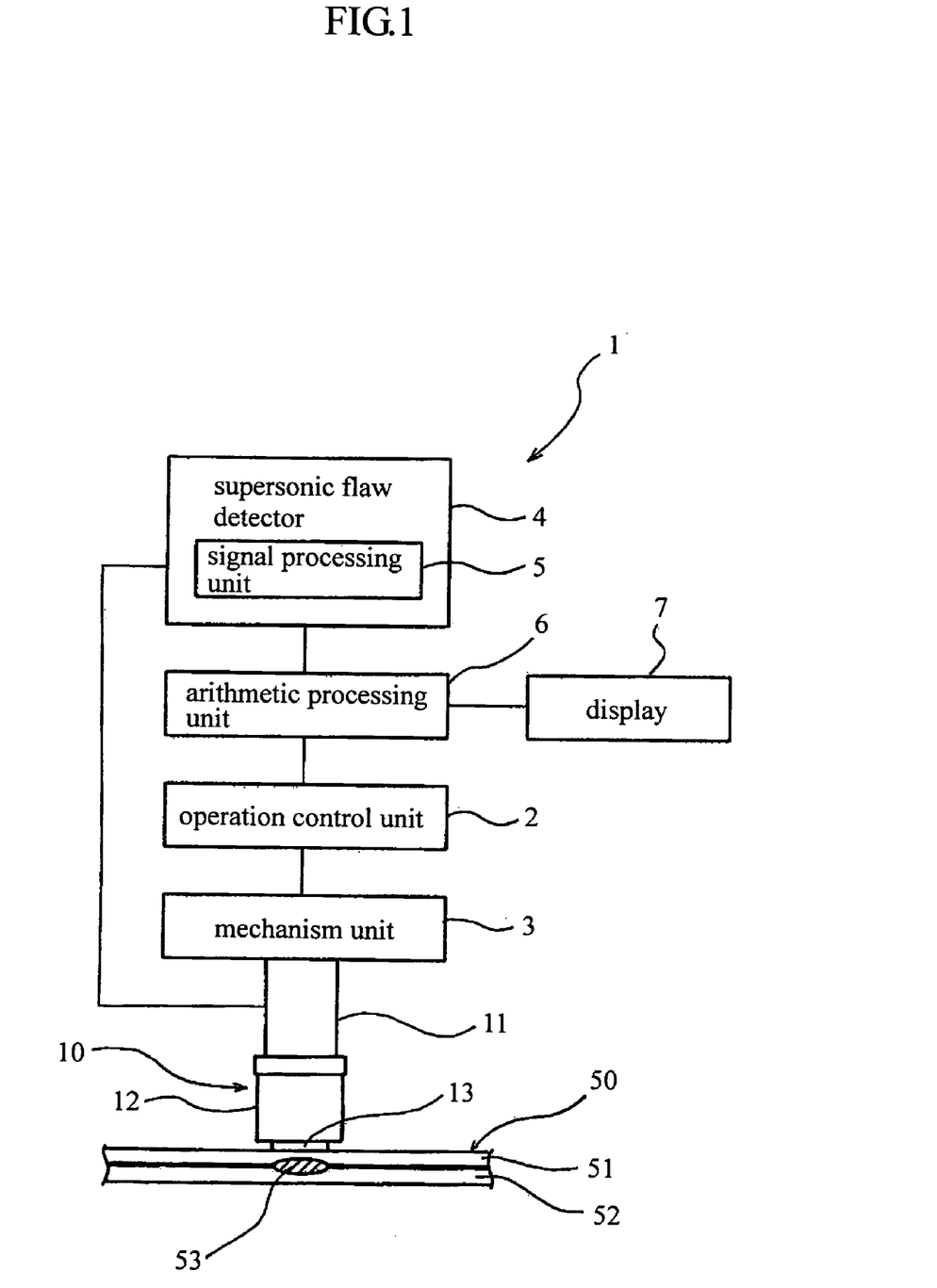
FIG. 1 is a diagram of a supersonic non-destructive apparatus with a supersonic sensor head as a first embodiment of the present invention.

A first embodiment of a supersonic sensor head for a supersonic non-detective test apparatus according to the present invention will be explained by referring to FIGS. 1 and 2. FIG. 1 is a schematic diagram for explaining a supersonic non-destructive test apparatus 1, and FIG. 2 is a cross section for showing the supersonic sensor head in FIG. 1.

In the supersonic non-destructive test apparatus 1, a sensor head 10 with a supersonic vibrator 11 causes a mechanism unit 3 to move based on a control signal transmitted from an operation control unit 2. Then, the supersonic sensor head 10 is pressed against a surface of a test object 50. In this state, a supersonic wave is transmitted from a supersonic flaw detector 4 to a supersonic vibrator 11 of the supersonic sensor head 10 through a signal treatment unit 5 in the supersonic flaw detector 4 and an arithmetic processing unit 6. The supersonic wave is output from the vibrator 11 to the test object 50 and the reflection of the supersonic wave is received by the supersonic vibrator 11 as a reflection echo. The reflection echo, i.e., the shape of the wave is shown as a diagram in a display 7.

Figure 2:
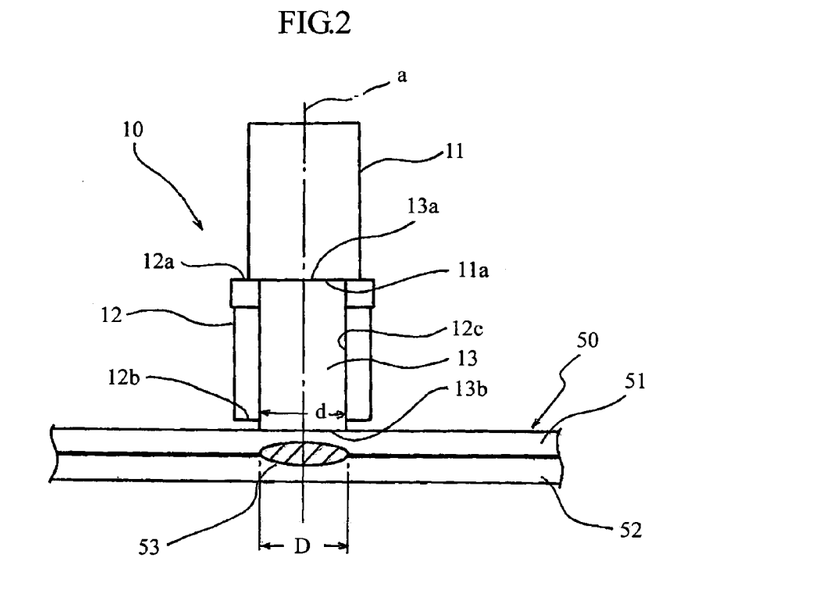
FIG. 2 is a cross section of a supersonic sensor head according to the present invention shown in FIG. 1.

The test object 50 has a welded structure obtained from a plate 51 and a plate 52 by spot welding at a welded part 53, as shown by the cross section in FIG. 2. By measuring the nugget diameter D of the welded part 53, the quality of the welding, that is, the stability of the weld is determined.

The supersonic sensor head 10 is composed of the supersonic vibrator 11 in the shape of a column having a flat free end 11a, and a holder 12 in the shape of a tube. The holder 12 is provided under the supersonic vibrator 11 so as to be coaxial therewith. A base end 12a of the holder 12 is connected to the free end of the vibrator 11. The holder 12 is made of a material which makes it difficult for a supersonic wave to be transmitted therethrough. The holder 12 has an opening end 12a with an inner diameter d which is approximately the same as the nugget diameter D of the welded part 53 to be detected.

A contact medium 13 made from a soft gel material is provided in the holder 12. The contact medium 13 is in the form of a column having a diameter approximately the same as the inner diameter 12c of the holder 12. The contact medium has a flat basal part 13a and a flat contact part 13b. The basal part 13a closely contacts the free end 11a of the supersonic vibrator 11, and the contact part 13b slightly protrudes from the opening end 12b of the holder 12. A supersonic sensor head 10 functions to press the contact part 13b of the contact medium 13 against the test object 50.

Accordingly, the contact medium 13 comes into close contact with a basal part 13a of the contact medium 13 by the compression deformation of the contact medium 13 within the holder 12. The holder restricts a diameter enlarging deformation of the contact part 13a of the contact medium 13. Therefore, it is possible to maintain the diameter of the contact part 13a to have approximately the same size as the inner diameter d of the opening end 12b of the holder 12. Namely, the inner diameter d can be maintained to be approximately the same as the nugget diameter D.

The contact medium 13 is made, for example, of a silicone rubber which is in a soft gel state and has an excellent softness and adhesion. The contact medium 13 is easily deformed by application of a small pressure by the sensor head 10, whereby it is possible to easily obtain a close contact state between the free end 11a of the supersonic vibrator 11 and a flat basal part 13a of the contact medium 13, and between the contact part 13b of the contact medium 13 and the test object 50.

A non-destructive test is carried out, as will be described below, with respect to the welded part 53 of the test object 50. The supersonic non-destructive test apparatus 1 including the supersonic sensor head 10 is used in the test.

According to a pre-set program, a control signal is output from an operation control unit 2. The control signal causes a mechanism unit 3 to change the position. Then, the contact part 13b of the contact medium 13 protruded from the opening end 12b presses a surface portion of the plate 51 corresponding to the welded part 53 in the test object 50. The pressure imparts compression deformation to the contact medium 13 in the holder 12. By the deformation, the free end 11a of the supersonic vibrator 11 comes in a close contact with the basal part 13 of the contact medium 13, and the contact part 13b of the contact medium 13, with the plate 51. In this state, the contact part 13a of the contact medium 13 is maintained to have approximately the same diameter as the inner diameter d of the opening end 12b of the holder 12, and hence as the predetermined nugget diameter D in the welded part 53. This is because the holder 12 restricts the diameter enlarging deformation of the contact part 13b.

In the state where the contact part 13b of the contact medium 13 is pressed to the plate 51, a supersonic wave is transmitted from the supersonic flaw detector 4 to the supersonic vibrator 11 of the supersonic sensor head 10. The supersonic wave is propagated between the supersonic vibrator 11 and the test object 50 through the contact medium 13. Here, the basal part 13a of the contact medium 13 is in a close contact with the free end 11a of the supersonic vibrator 11, and the contact part 13b of the contact medium 13 is in a close contact with the plate 51. A reflection echo is received by the supersonic vibrator 11.

With the above-mentioned configuration, the supersonic wave is propagated from the supersonic vibrator 11 to the test object 50 by passing through the contact medium 13. The supersonic wave is converged in the range of the nugget diameter D. In other words, it is possible to prevent the supersonic wave from diverging excessively beyond the nugget diameter D.

The reflection echo of the supersonic wave is shown as a diagram in a display 7. Based on the nugget diameter D corresponding to the state of the welded part 53 shown in the display 7, it is possible to determine the stability of the welded part 53.

For instance, when the nugget diameter D of the welded part 53 is smaller compared with a desired nugget diameter, it is possible that connection strength has not been sufficiently obtained between the plates 51 and 52. Moreover, when the figure shows that the nugget contains a discontinuous part, it is also possible to cause lowering the connection strength in the welded part 53.

When the test is completed, the transmission of the supersonic wave from the supersonic flaw detector 4 to the supersonic vibrator 11 is suspended. Thereafter, the mechanism unit 3 is caused to move for raising a supersonic sensor head 10. The contact medium 13 is raised together with the contact medium 13 and is released from the compression deformation. Then, the contact medium 13 detached from the plate 51 is restored by the elastic restoring force, by loosing the contact between the surface of the plate 51 and the contact part 13b of the contact medium 13. Likewise, the elastic restoring force of the contact medium 13 makes the free end 11a of the supersonic vibrator 11 to be detached from the basal part 13a of the contact medium 13.

It is possible to stably attain the test accuracy by the supersonic sensor head 10 with the simple structure as mentioned above. The contact medium 13 contained in the holder can be repeatedly used for a long time, since excessive deformation of the medium is restrained and the durability is maintained. Therefore, it is possible to reduce running cost of the test apparatus.

(Second Embodiment)

Figure 3:
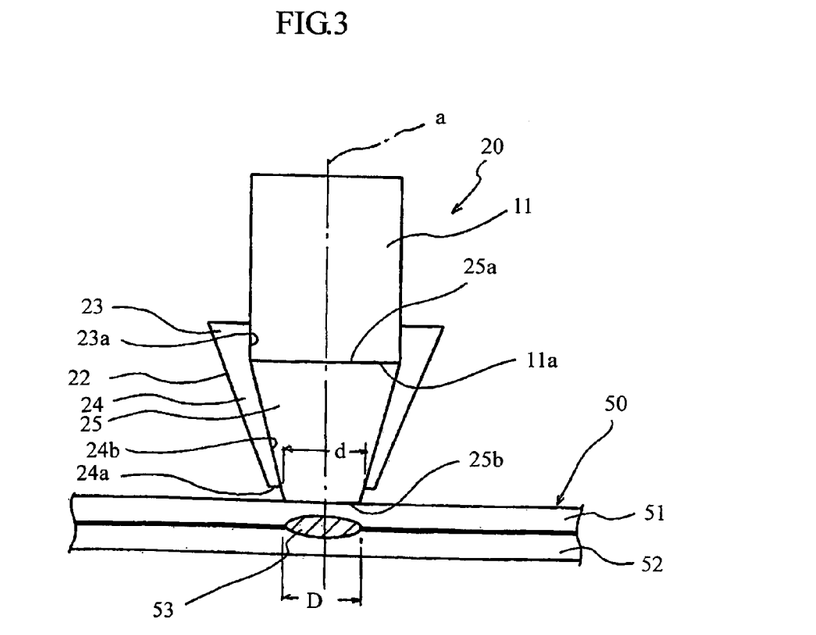
FIG. 3 is schematic cross section of a supersonic sensor head as a second embodiment of the present invention.

FIG. 3 is a schematic cross section for explaining a supersonic sensor head as a second embodiment. Structural parts in FIG. 3 corresponding to those in FIG. 2 are shown with the same reference numerals in both the figures, and the explanation on the corresponding parts will be omitted.

A supersonic sensor head 20 in the second embodiment is in the form of a column having a flat free end 11a, as in the first embodiment. A holder 22 is provided coaxially with a supersonic vibrator 11 with being connected to the free end 11a of the supersonic vibrator 11. The holder 22 is detachably connected to the outer periphery of the supersonic vibrator 11 at a lower position thereof. The holder 22 contains a contact medium 25 therein, similar to the first embodiment. The contact medium 25 is also made of a gel material such as a silicone rubber. The holder 22 is made of a material which makes it difficult for a supersonic wave to be transmitted therethrough. The holder 22 has a base part 23 and a conical tube part 24 which is integral with the base part 23. The base part 23 is in the form of a ring having a relatively large diameter compared to the rest of the holder 23. The base part 23 has an inner surface 23a which contacts the outer periphery of the supersonic vibrator 11, when the holder 22 is connected to the vibrator 11. The conical tube part 24 has one end which is integral with the base part 23, and an opening end 24a as another end. The diameter of the conical tube part 24 gradually decreases toward the opening end 24a. The conical tube has a conically tapered inner surface 24b. The inner surface 24b of the holder 22 is made of a material which makes it difficult for the supersonic wave to be transmitted therethrough. Therefore, the holder 22 helps to converge the supersonic wave toward the opening end 24a. The opening end 24a has an inner diameter d which is approximately the same as the predetermined nugget diameter D of the welded part 53 in the test object 50.

The contact medium 25 approximately in a conical shape is contained in the holder 22 with the outer surface fitting with the inner surface 24b of the holder 22. The contact medium 25 has a flat basal part 25a and a contact part 25b. The basal part 25b contacts the free end 11a of the supersonic vibrator 11, which slightly protrudes from the opening end 24a of the holder 22.

A non-destructive test is carried out with respect to the welded part 53 of the test object 50 by using the supersonic non-destructive test apparatus 1 having the supersonic sensor head 20.

According to a pre-set program, the contact part 25b of the contact medium 25 protruded from the opening end 24a of the holder 22 presses a surface portion of the plate 51 corresponding to the welded part 53 in the test object 50, as shown in FIG. 3. The pressure application makes the contact medium 25 easily deform within the holder 22. By the deformation, the free end 11a of the supersonic vibrator 11 comes in a close contact with the basal part 25a of the contact medium 25, and the contact part 25b of the contact medium 25 with the test object 50. The holder 22 restricts the diameter enlarging deformation of the contact part 25b. In this state, the contact part 25b of the contact medium 25 is maintained to have approximately the same diameter as the inner diameter d of the opening end 24a of the conical tube part 24. In other words, the contact part 25b of the contact medium 25 is maintained to have the same diameter as of the nugget diameter D.

In the state where the contact part 25b of the contact medium 25 is pressed against the plate 51, a supersonic wave is propagated between the supersonic vibrator 11 and the test object 50. Here, the supersonic wave is transmitted from supersonic vibrator 11 to the test object 50 through the contact medium 25, which is closely in contact with the vibrator 11 and with the plate 51. The supersonic wave is converged to the width of the inner diameter d of the opening end 24a of the tube part 24 in the holder 20, namely to the nugget diameter D (test diameter) of the welded part 53. The reflection echo from the test object 50 is received by the supersonic vibrator 11. Based on the reflection echo, the stability of the weld is determined According to the supersonic sensor head 20 of the present invention wherein the holder 22 and the contact medium 25 are formed in conical shapes, the contact medium 25 made from the soft gel material is stably maintained in the holder 22. It is possible to replace the holder with other holders having various inner diameters d corresponding to the various nugget diameters D. In other words, it is possible to carry out the non-destructive test only by exchanging the holders, not by preparing many kinds of expensive supersonic vibrators with different sizes. By the supersonic vibrator 11 for general use as in the invention and equipment investment will be minimized.

For detachably connecting the holder 22 to the supersonic vibrator 11, it is also possible to use a clamp apparatus or a screw mechanism.

(Third Embodiment)

Figure 4A:
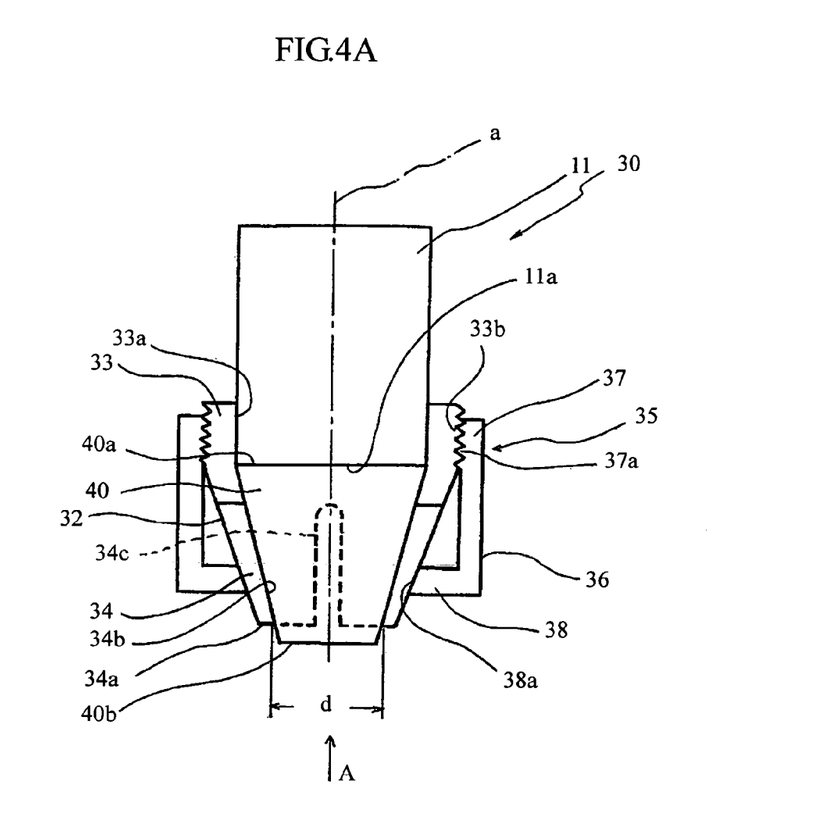
FIG. 4A is a cross section of a supersonic sensor head as a third embodiment of the present invention.
Figure 4B:
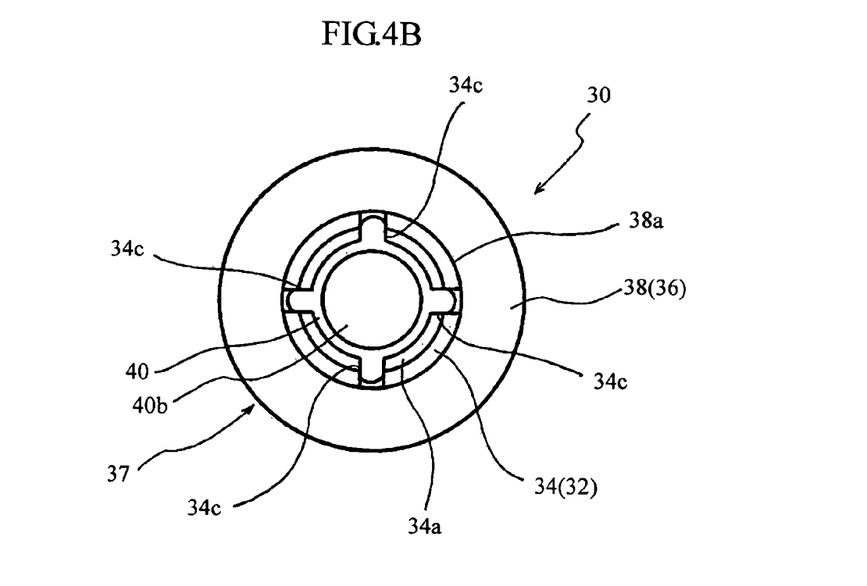
FIG. 4B is a diagram of the supersonic sensor head shown in FIG. 4A seen in the direction of an arrow A as shown in FIG. 4A.

FIGS. 4A and 4B are schematic diagrams for explaining the supersonic sensor head as a third embodiment of the present invention. FIG. 4A is a cross section of the supersonic sensor head, and FIG. 4B is a diagram of the supersonic sensor head obtained by viewing FIG. 4A in the direction of an arrow A in FIG. 4A. Structural parts in FIG. 4 corresponding to those in FIGS. 2 and 3 are shown with the same reference numerals therein and the explanation on the corresponding parts will be omitted.

A supersonic sensor head 30 in the third embodiment is in the form of a column having a flat free end 11a as in the first embodiment. A holder 32 with a converging mechanism 35 is provided coaxially with the supersonic vibrator 11 with respect to an axis a, by being connected to the free end 11a of the supersonic vibrator 11. The holder 32 contains a contact medium 40 therein, similar to the first embodiment. The contact medium 40 is also made from a gel material such as a silicone rubber.

The holder 32 is made of a material which makes it difficult for a supersonic wave to be transmitted therethrough. The holder 32 has a base part 33 and a conical tube part 34 which is integral with the base part 33. The base part 33 is in the form of a ring having a relatively large diameter compared to the rest of the holder 32 and is detachable from the supersonic vibrator 11. The base part 33 has an inner surface 23a which contacts the outer periphery of the supersonic vibrator 11, when the holder 32 is connected to the vibrator 11. The conical tube part 34 has one end which is integral with the base part 33, and an opening end 34a as another end. The diameter of the conical tube part 34a gradually decreases toward the opening end 34a. The conical tube part 34 has a conically tapered inner surface 34b. A plurality of slits 34c is formed in the tube part 34. The slits 34c extend in an axial direction from the opening end 34a of the tube part 34.

The diameter converging mechanism 35 has an operation part 36 which is approximately in the form of a cylinder. The operation part 36 includes a base portion 37 and a ring portion 38 formed integrally with the base portion 37. The base portion 37 is in the form of a ring with a screw hole 37a for receiving the holder 32. Therefore, the base portion 37 of the diameter converging mechanism 35 can be connected with the screw part 33a formed around the base portion 37 of the holder 32. A peripheral surface 38a of the ring portion 38 in the converging mechanism 35 is in contact with the outer periphery of the tube part 34 of the holder 32. The screw part 33b and the screw hole 37a can be connected to each other by rotating the base portion 37 in the converging mechanism 35 on the base part 33 of the holder 32. The screw part 33b and the screw hole 37a constitute a screw mechanism. When the outer periphery of the tube part 34 is moved downwardly in the direction of the opening end 34a by rotating the operation part 36 of the converging mechanism 35 on the ring portion 38, the diameter of the opening end 34a is increased. The slits 34c, which divide the tube part 34 into a plurality of sections, allow the opening end 34a to increase the diameter. When the operation part 36 is rotated in a reversed direction, the tube part 34 is being moved upwardly by means of the screw mechanism. In this case, the diameter of the opening end 34a decreases by the closure of the slits 34a. Thus, the converging mechanism 35 enlarges and reduces the diameter of the inner diameter d of the opening end 34a. The converging mechanism 35 includes the slits 34c, and the operation part 36 including the base part 37 and the ring part 38.

By using the thus structured converging mechanism 35, the inner diameter d of the opening end 34 in the holder 32 is adjusted so as to have approximately the same diameter with as the nugget diameter D of the welded part 53 in the test object 50.

The contact medium 40 is also approximately in the shape of a cone which has an outer surface so that the outer surface fits the conically tapered inner surface 34b of the holder 32. The contact medium 40 includes a flat basal part 40a and the contact part 40b. The flat basal part 40a contacts the free end 11a of the supersonic vibrator 11, and the contact part 40b slightly protrudes from the opening end 34a of the holder 32.

In the supersonic sensor head 30 with the converging mechanism 35, the contact medium 40 made of the soft gel material can be maintained in the holder 32 in a conical shape. The converging mechanism 35 adjusts the inner diameter d of the opening end 34a of the holder 32 to be the same as the nugget diameter D of the welded part of the test object prior to a test. Therefore, the supersonic head 30 of the invention can be used for non-destructive tests on many kinds of test objects with different nugget diameters.

The structure of the converging mechanism 35 is not limited to the above embodiment. For example, it is possible to use a ring-shaped clamp which expands and contracts over the outer surface of the tube part 34, and that the outer surface has slits for dividing the outer surface into several sections.

In addition to the above embodiment, it is possible to use the supersonic sensor head of the present invention for a non-destructive test for testing defects in many kinds of structures.

The present invention being thus described, it will be clearly understood that the same may be varied in many ways. Such variations are not to be regarded as a departure from the spirit and scope of the present invention, and all such modification as would be easily understood to one skilled in the art are intended to be included within the scope of the appended claims.

What is claimed is:

1. A supersonic sensor head for a supersonic non-destructive test apparatus for measuring shapes of supersonic waves transmitted in a test object, comprising:
    a supersonic vibrator for transmitting and receiving supersonic waves;
    a tube-shaped holder having a base end and an opening end, the holder being coaxial with the supersonic vibrator so that the base end of the holder is in contact with a free end of the supersonic vibrator; and
    a contact medium made of a soft gel material provided between the supersonic vibrator and the test object, so that the supersonic vibrator indirectly contacts the test object, the contact medium having a basal part and a contact part, and being contained in the holder, the basal part contacting the free end of the supersonic vibrator and the contact part protruding from the opening end of the holder, a pressure applied between the contact part of the contact medium and the test object urging the free end of the supersonic vibrator to closely contact the basal part of the contact medium, and the contact part of the contact medium to closely contact the test object,
    wherein the tube-shaped holder has a diameter converging mechanism for regulating the inner diameter of the tube-shaped holder at the opening end thereof.

2. The supersonic sensor head for a supersonic non-destructive test apparatus as claimed in claim 1, wherein the holder is approximately cone-shaped, the inner diameter of the cone decreasing from the base end to the opening end.

3. The supersonic sensor head for a supersonic non-destructive test apparatus as claimed in claim 2, wherein the inner diameter of the holder at the opening end is approximately the same as a test diameter of the test object.

4. The supersonic sensor head for a supersonic non-destructive test apparatus as claimed in claim 2, wherein the base end of the holder is detachably connected to the supersonic vibrator.

5. The supersonic sensor head for a supersonic non-destructive test apparatus as claimed in claim 2, wherein the soft gel material is a silicone rubber.

6. The supersonic sensor head for a supersonic non-destructive test apparatus as claimed in claim 1, wherein the inner diameter of the holder at the opening end is approximately the same as a test diameter of the test object.

7. The supersonic sensor head for a supersonic nondestructive test apparatus as claimed in claim 6, wherein the base end of the holder is detachably connected to the supersonic vibrator.

8. The supersonic sensor head for a supersonic nondestructive test apparatus as claimed in claim 6, wherein the soft gel material is a silicone rubber.

9. The supersonic sensor head for a supersonic nondestructive test apparatus as claimed in claim 1, wherein the base end of the holder is detachably connected to the supersonic vibrator.

10. The supersonic sensor head for a supersonic nondestructive test apparatus as claimed in claim 9, wherein the soft gel material is a silicone rubber.

11. The supersonic sensor head for a supersonic nondestructive test apparatus as claimed in claim 1, wherein the soft gel material is a silicone rubber.

12. The supersonic sensor head for a supersonic nondestructive test apparatus as claimed in claim 1, wherein the diameter converging mechanism enlarges and reduces the inner diameter of the tube-like holder at the opening end thereof.

13. The supersonic sensor head for a supersonic nondestructive test apparatus as claimed in claim 1, wherein the tube-like holder has a slit extending in an axial direction of the tube-like holder.

14. The supersonic sensor head for a supersonic nondestructive test apparatus as claimed in claim 1, wherein the tube-like holder has a base part and a regulating part.

15. The supersonic sensor head for a supersonic nondestructive test apparatus as claimed in claim 14, wherein the diameter converging mechanism has an operation part, the operation part comprises:
 a base portion contacting with the base part of the tube-like holder, and
 a contact portion contacting with the regulating part of the tube-like holder.

16. The supersonic sensor head for a supersonic nondestructive test apparatus as claimed in claim 15, wherein the contact portion moves in an axial direction of the tube-like holder.

17. The supersonic sensor head for a supersonic nondestructive test apparatus as claimed in claim 16, wherein the contact portion moves in an axial direction of the tube-like holder by rotating the operation part.

18. The supersonic sensor head for a supersonic nondestructive test apparatus as claimed in claim 15, wherein the base portion and the base part constitute a screw mechanism.

19. The supersonic sensor head for a supersonic nondestructive test apparatus as claimed in claim 14, wherein the regulating part has a conical surface.

20. A method for conducting a supersonic non-destructive test for measuring shapes of supersonic waves transmitted in a test object, comprising:
 providing a tube-shaped holder having a base end and an opening end, the holder being coaxial with the supersonic vibrator so that the base end of the holder is in contact with a free end of the supersonic vibrator;
 positioning a contact medium made of a soft gel material between the supersonic vibrator and the test object, so that the supersonic vibrator indirectly contacts the test object, the contact medium having a basal part and a contact part, and being contained in the holder;
 contacting the basal part with the free end of the supersonic vibrator and arranging the contact part to protrude from the opening end of the holder;
 applying pressure between the contact part of the contact medium and the test object thereby urging the free end of the supersonic vibrator to closely contact the basal part of the contact medium, and the contact part of the contact medium to closely contact the test object, and
 transmitting; and receiving supersonic waves from a supersonic vibrator,
 wherein the tube-shaped holder has a diameter converging mechanism for regulating the inner diameter of the tube-shaped holder at the opening end thereof.

* * * * *